United States Patent
Yoshizawa et al.

(10) Patent No.: US 12,345,787 B2
(45) Date of Patent: Jul. 1, 2025

(54) MAGNETIC RESONANCE IMAGING APPARATUS AND CONTROL METHOD THEREOF

(71) Applicant: FUJIFILM Healthcare Corporation, Kashiwa (JP)

(72) Inventors: Nobuyuki Yoshizawa, Chiba (JP); Yoshitaka Bito, Chiba (JP); Takashi Nishihara, Chiba (JP)

(73) Assignee: FUJIFILM Corporation, Tokyo (JP)

(*) Notice: Subject to any disclaimer, the term of this patent is extended or adjusted under 35 U.S.C. 154(b) by 176 days.

(21) Appl. No.: 18/138,210

(22) Filed: Apr. 24, 2023

(65) Prior Publication Data
US 2023/0349995 A1  Nov. 2, 2023

(30) Foreign Application Priority Data
Apr. 27, 2022  (JP) .................. 2022-073311

(51) Int. Cl.
*G01R 33/54* (2006.01)
*G01R 33/56* (2006.01)

(52) U.S. Cl.
CPC ....... *G01R 33/546* (2013.01); *G01R 33/5601* (2013.01); *G01R 33/5602* (2013.01); *G01R 33/5607* (2013.01)

(58) Field of Classification Search
CPC .............. G01R 33/546; G01R 33/5601; G01R 33/5635; G01R 33/56366; G01R 33/5602; G01R 33/56325; G01R 33/5607; G01R 33/448; G01R 33/50; A61B 5/055; A61B 5/0033
See application file for complete search history.

(56) References Cited

U.S. PATENT DOCUMENTS

| | | | |
|---|---|---|---|
| 2012/0003160 A1* | 1/2012 | Wolf | B82Y 5/00 424/9.3 |
| 2019/0056470 A1* | 2/2019 | Wang | G01R 33/5601 |
| 2024/0225448 A1* | 7/2024 | Schuetz | A61B 5/4244 |

OTHER PUBLICATIONS

Yuko Nakamura et al., "Pseudo-random Trajectory Scanning Suppresses Motion Artifacts on Gadoxetic Acid-enhanced Hepatobiliary-phase Magnetic Resonance Images", Magn. Reson. Med. Sci. doi:10.2463/mrms.mp.2018-0174.

Nakayama T. et al., "Balanced MR cholangiopancreatography with motion-sensitized driven-equilibrium (MSDE) preparation: feasibility of Gd-EOB-DTPA-enhanced biliary examination", Clin. Radiol. Dec. 2016. 71(12):1284-1288.

(Continued)

*Primary Examiner* — Rishi R Patel
(74) *Attorney, Agent, or Firm* — Paul Teng

(57) ABSTRACT

In contrast-enhanced MRI, a visualization capability of a tissue which a contrast agent reaches is increased, and overall imaging time is shortened. An imaging unit of an MRI apparatus includes a gradient echo pulse sequence for acquiring a T1 weighted image including a fat saturation pulse, and a control unit performs control to generate images of a plurality of phases having different arrival positions of a contrast agent by repeating the pulse sequence for a predetermined time from administration of the contrast agent to the subject by the imaging unit. At this time, a preparation pulse that suppresses a signal from a contrast agent present outside a target tissue (cell) is added prior to a pulse sequence, in a phase immediately before reaching the target tissue.

13 Claims, 16 Drawing Sheets

(56) References Cited

OTHER PUBLICATIONS

European search report dated Sep. 18, 2023 in connection with European Patent Application No. 23 17 0267.
Ohno, T., et al., "Usefulness of breath-hold inversion recovery-prepared T1-weighted two-dimensional gradient echo sequence for detection of hepatocellular carcinoma in Gd-EOB-DTPA-enhanced MR imaging," Clinical Imaging, vol. 40, No. 5, pp. 997-1003 (May 13, 2013).

* cited by examiner

MAGNETIC RESONANCE IMAGING APPARATUS AND CONTROL METHOD THEREOF

BACKGROUND OF THE INVENTION

1. Field of the Invention

The present invention relates to a magnetic resonance imaging apparatus (hereinafter, abbreviated as "MRI apparatus"), and particularly, to a control technique for an MRI apparatus in MRI examination using a contrast agent.

2. Related Art

An MRI apparatus is an image diagnostic apparatus that collects a signal generated by nuclear magnetic resonance from a tissue to be examined and images the signal, and can suppress a signal from the tissue unnecessary for diagnosis by varying a pulse sequence and an imaging condition and generate various weighted images with different contrasts.

For example, in diagnosis of hepatocellular carcinoma, there is a method of suppressing a signal from a hepatocyte extracellular space by using intra-voxel incoherent motion imaging (IVIM) using a diffusion weighted image (DWI) sequence. However, since the pulse sequence serving as a base of the IVIM is spin echo system echo planar (SE-EPI), echo time (TE) is extended, a signal of an interstitial fluid having a long relaxation time T2 of transverse magnetization is increased, and a signal in a cell having a short T2 is decreased. Therefore, contrast of an obtained image is low, and diagnostic performance is low.

To cope with this issue, an imaging method is also developed in which contrast agents are combined to improve the diagnostic performance by using a difference in absorption and residence time of the contrast agents depending on the tissue. As an example, in the diagnosis of the hepatocellular carcinoma, continuous imaging (dynamic MRI) is performed from administration of the contrast agent until the contrast agent remains in hepatocytes using the contrast agent such as gadolinium ethoxybenzyl diethlenetriamine pentaacetic acid (Gd-EOB-DTPA, hereinafter, abbreviated as EOB), and an image in which a normal tissue of the hepatocytes and a cancer can be clearly distinguished is acquired (NPL 1).

In the method, by acquiring an image of each phase from an artery to a liver tissue via portal vein after the contrast agent is administered, information on the cancer can be known in detail from an image of a phase (arterial phase) in a relatively early stage in which the contrast agent is absorbed into the cancer from the artery which is a nutrient blood vessel of the cancer and an image of a phase (hepatobiliary phase) in a later stage in which the contrast agent reaches and stays at the hepatocytes via the artery and the portal vein.

Further, in the MRI, there are several methods for suppressing the signal from a tissue other than a target tissue, and the methods are also applied to contrast-enhanced MRI. For example, in a technique described in NPL 1, during the imaging, fat saturation is performed to improve a visualization capability of hepatocytes. NPL 2 discloses that, in order to suppress signals of an artery and portal vein in gallbladder imaging in which T2 weighted is important, a motion-sensitized driven-equilibrium (MSDE) pulse is used. However, a technique described in NPL 2 is based on T2 weighted imaging, and cannot be applied to liver cancer diagnosis for tracking motion of the contrast agent from the image of each phase as described above.

CITATION LIST

Non-Patent Literature

NPL 1: "Pseudo-random Trajectory Scanning Suppresses Motion Artifacts on Gadoxetic Acid-enhanced Hepatobiliary-phase Magnetic Resonance Images" Yuko Nakamura et al, Magn. Reson. Med. Sci. doi:10.2463/mrms.mp.2018-0174 NPL 2: "Balanced MR cholangiopancreatography with motion-sensitized driven-equilibrium (MSDE) preparation: feasibility of Gd-EOB-DTPA-enhanced biliary examination" Nakayama T. et al, Clin. Radiol. 2016 December 71(12):1284-1288

SUMMARY OF THE INVENTION

In general, time for a contrast agent to be taken into the hepatocytes after administration and for a contrast agent not taken into the hepatocytes to be discharged is about 20 minutes. However, it takes time for a patient having a decreased liver function to take in and discharge the contrast agent. Therefore, while in general, it is said that a hepatobiliary phase occurs 20 minutes later, it cannot be determined whether the hepatobiliary phase actually occurs even 20 minutes later. When the contrast agent that has not been incorporated into the hepatocytes is present, that is, when the contrast agent is present in a hepatocyte extracellular space such as an interstitial fluid and a blood vessel, since only a tumor cannot be rendered with high luminance, there is a problem that diagnostic performance is degraded. Further, there is a problem that it takes considerable time when imaging up to the hepatobiliary phase should be accomplished for all subjects including the patient who takes time to take the contrast agent.

An object of the invention is to provide an image excellent in diagnostic performance in a relatively short time while shortening examination time lengthened depending on arrival time of a contrast agent in MRI using the contrast agent.

In order to solve the above problem, the invention performs imaging continuously over a plurality of phases and, during the imaging, adds a pulse for suppressing a contrast agent signal in a tissue (for example, a moving region such as a hepatocyte extracellular space) around a target tissue in imaging of a phase after a lapse of a predetermined number of phases from start of imaging.

That is, the MRI apparatus of the invention includes an imaging unit that applies a high-frequency magnetic field and a gradient magnetic field to a subject, collects a nuclear magnetic resonance signal generated from the subject, and generates an image of the subject, and a control unit that controls the imaging unit. The control unit performs control to generate images of a plurality of phases having different arrival positions of the contrast agent by repeating a pulse sequence for a predetermined time from administration of the contrast agent to the subject by the imaging unit. At this time, a preparation pulse for suppressing a signal from the contrast agent present outside an arrival target tissue (cell) of the contrast agent is added prior to the pulse sequence in a part of the plurality of phases. The pulse sequence executed by the imaging unit is, for example, a pulse sequence for acquiring a T1 weighted image including a fat saturation pulse.

A control method for a magnetic resonance imaging apparatus of the invention is a control method for an MRI apparatus that applies a high-frequency magnetic field and a gradient magnetic field to a subject according to a pulse sequence, collects a nuclear magnetic resonance signal generated from the subject, and generates an image of the subject. The control method includes: using a pulse sequence for acquiring a T1 weighted image including a fat saturation pulse to repeat the pulse sequence for a predetermined period of time from administration of a contrast agent to the subject to generate images of a plurality of phases having different arrival positions of the contrast agent; and adding a preparation pulse configured to suppress a signal from the contrast agent present outside an arrival target tissue (cell) of the contrast agent prior to the pulse sequence, in a part of the plurality of phases.

According to the invention, it is possible to suppress the signal in a region including the contrast agent present around the target tissue in a predetermined phase while the contrast agent reaches the target tissue. Accordingly, it is possible to obtain an image capable of clearly identifying the target tissue and the other tissues without waiting for imaging of a phase in which most of the contrast agent reaches the target tissue, and it is possible to obtain an image having the excellent diagnostic performance in a short time.

The invention is applied to, for example, a contrast-enhanced MRI in which hepatocytes are set as an arrival target tissue, and a liver can be rendered with high contrast, and thus the diagnostic performance of a tumor in the liver can be improved. At this time, an image having a contrast that is equivalent to the contrast in the hepatobiliary phase can be obtained in a portal venous phase or a transitional phase, and thus the examination time can be shortened. Further, information useful for evaluating the liver function can be obtained.

DESCRIPTION OF EMBODIMENTS

Hereinafter, embodiments of an MRI apparatus according to the invention will be described with reference to the drawings.

First, an overall configuration of an MRI apparatus to which the invention is applied will be described.

Configuration of MRI Apparatus

Figure 1:
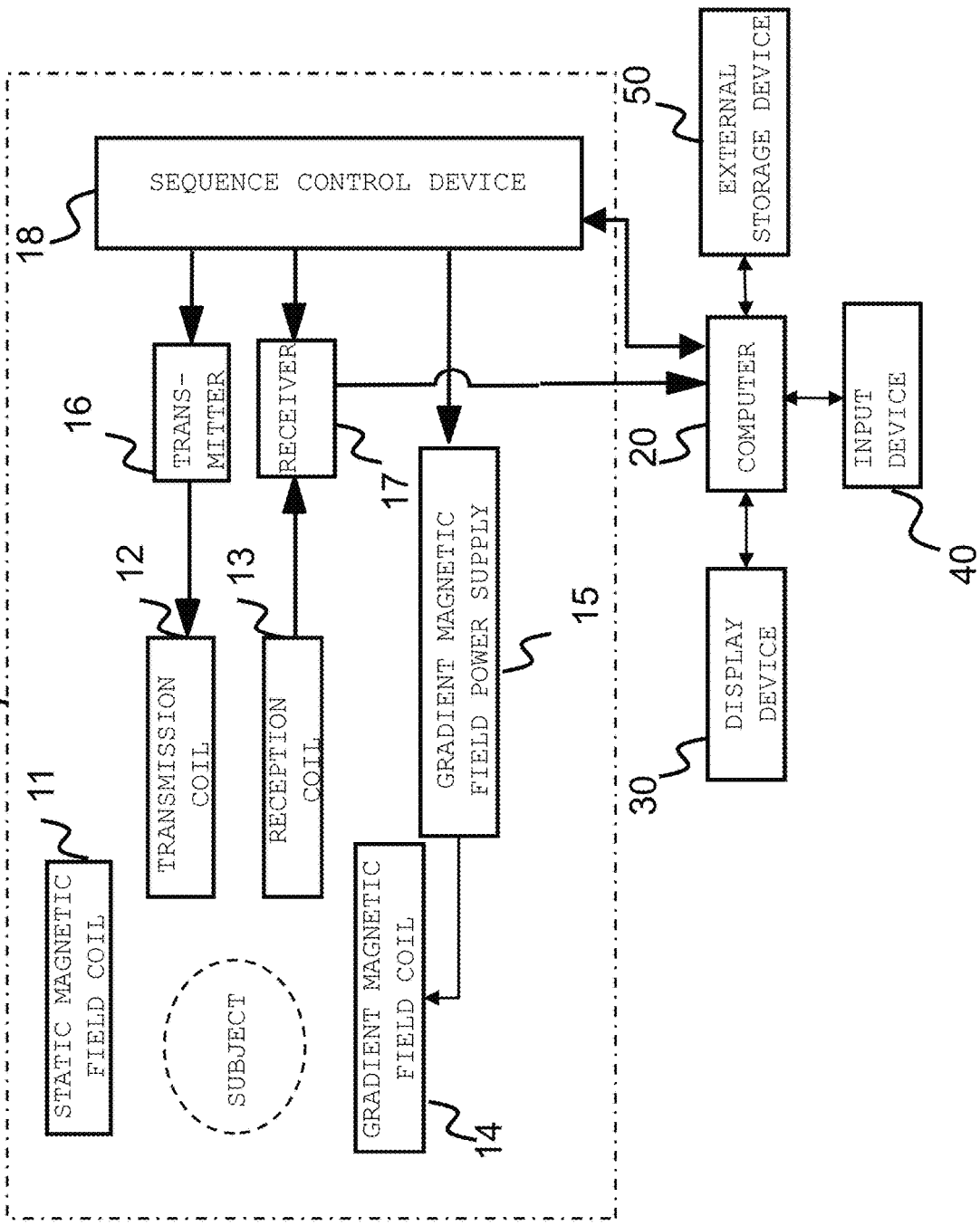
FIG. 1 is a diagram showing an overall configuration of an MRI apparatus to which the invention is applied.

As shown in FIG. 1, an MRI apparatus 1 of the present embodiment includes a static magnetic field generation unit such as a static magnetic field coil 11 that generates a static magnetic field in a space in which a subject is placed, a transmission high-frequency coil 12 (hereinafter, simply referred to as a transmission coil) and a transmitter 16 that transmit a high-frequency magnetic field pulse (RF pulse) to a measurement region of the subject, a reception high-frequency coil 13 (hereinafter, simply referred to as a reception coil) and a receiver 17 that receive a nuclear magnetic resonance signal generated from the subject, a gradient magnetic field coil 14 that applies a magnetic field gradient to the static magnetic field generated by the static magnetic field coil 11 and a gradient magnetic field power supply 15 that is a drive power supply thereof, a sequence control device 18, and a computer 20. Units of the MRI apparatus 1 other than the computer 20 are collectively referred to as an imaging unit 10.

The MRI apparatus 1 has a vertical magnetic field type and a horizontal magnetic field type depending on a direction of the generated static magnetic field, and various forms of the static magnetic field coil 11 are adopted according to the type. The gradient magnetic field coil 14 includes a combination of a plurality of coils that generate gradient magnetic fields in three axial directions (x direction, y direction, and z direction) orthogonal to one another, and is driven by the gradient magnetic field power supply 15. By applying the gradient magnetic field, position information can be added to the nuclear magnetic resonance signal generated from the subject.

In the illustrated example, a case is illustrated in which the transmission coil 12 and the reception coil 13 are separate. In another case, one coil which functions as the transmission coil 12 and the reception coil 13 may be used. A high-frequency magnetic field applied by the transmission coil 12 is generated by the transmitter 16. The nuclear magnetic resonance signal detected by the reception coil 13 is sent to the computer 20 through the receiver 17.

The sequence control device 18 controls operations of the gradient magnetic field power supply 15, the transmitter 16, and the receiver 17, controls timings of application of the gradient magnetic field and the high-frequency magnetic field and reception of the nuclear magnetic resonance signal, and executes measurement. A time chart of control is called a pulse sequence, and the pulse sequence varies depending on an imaging method and is stored in advance in a storage device or the like provided in the computer 20. When the imaging method or an imaging part is determined, the sequence control device 18 performs control such that a predetermined pulse sequence is read out, an imaging sequence to be used for imaging is calculated using an imaging condition set by a user, and the imaging unit 10 collects the nuclear magnetic resonance signals according to the imaging sequence.

The computer 20 is an information processing apparatus including a CPU, a memory, a storage device, and the like, and has a function as a control unit that controls an operation of each unit of the MRI apparatus via the sequence control device 18 and a function as a calculation unit that performs arithmetic processing on a received echo signal. These functions are executed by the computer 20 reading a program stored in the storage device. However, a part of the functions may be implemented by a programmable IC such as an ASIC or an FPGA.

A display device 30, an input device 40, an external storage device 50, and the like are connected to the computer 20. The display device 30 is an interface that displays, to an operator, a result obtained by the arithmetic processing and the like. The input device 40 is an interface for the operator to input conditions, parameters, and the like necessary for the measurement and the arithmetic processing that are performed in the present embodiment. The user can input measurement parameters (imaging condition) such as the number of echoes to be measured, an echo time TE, and an echo interval ITE via the input device 40. The external storage device 50 stores data used for various types of arithmetic processing executed by the computer 20, data obtained by the arithmetic processing, received conditions, parameters, and the like, together with the storage device inside the computer 20.

Next, the pulse sequence used for imaging of the MRI apparatus of the present embodiment will be described.

Figure 2:
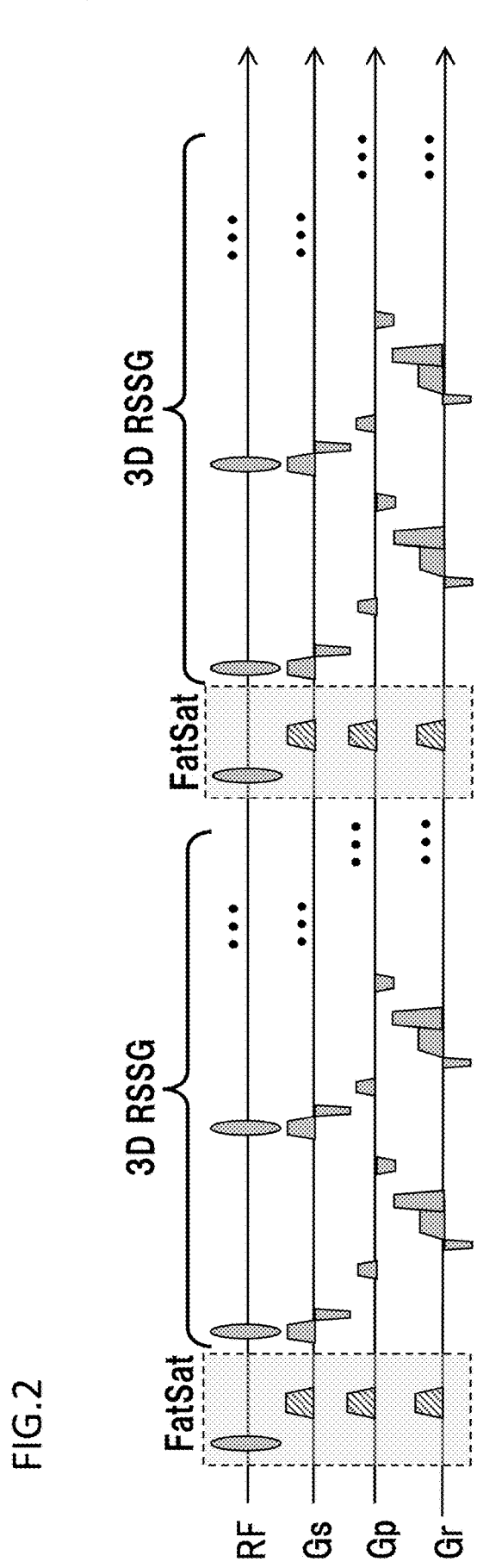
FIG. 2 is a diagram showing an example of a gradient echo pulse sequence including a fat saturation pulse.

In the present embodiment, as an example, a T1 weighted gradient echo pulse sequence (FatSat-RSSG: Rf-Spoiled Steady state Gradient echo) including a fat saturation pulse (referred to as FatSat pulse) is used. FIG. 2 shows an example of 3D FatSat-RSSG. In FIG. 2, RF denotes the RF pulse, and Gs, Gp, and Gr denote gradient magnetic field pulses in a slice direction, a phase encoding direction, and a readout direction, respectively.

In the pulse sequence, an RF pulse corresponding to a magnetic resonance frequency of fat is applied as the FatSat pulse, and a spoiler gradient magnetic field pulse is applied to start an RF spoiling gradient echo type pulse sequence in a state in which a signal from the fat is suppressed. An RSSG sequence measures gradient echoes generated by a readout gradient magnetic field Gr while varying an intensity of the phase encoding gradient magnetic field Gp. By repeating the sequence while changing the slice gradient magnetic field Gs, 3D measurement data is obtained. In the gradient echo pulse sequence, a T1 weighted image is obtained in which contrast of a tissue having a long longitudinal relaxation time T1 is weighted.

Figure 3:
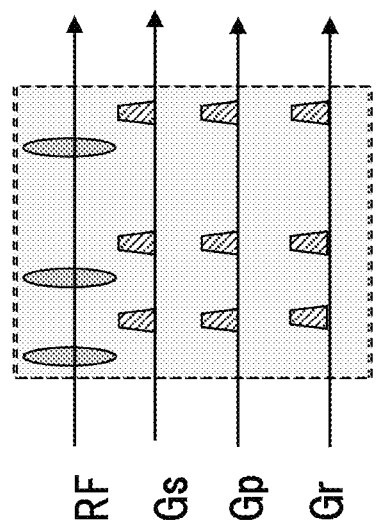
FIG. 3 is a diagram showing a modification of the fat saturation pulse.

In the example shown in FIG. 2, the FatSat pulse is inserted every time a 3D-RSSG is repeated, but instead of using the FatSat pulse every 3D-RSSG, the FatSat pulse may be inserted intermittently, that is, at a rate of once every several times. An example in which an RF pulse is used as the FatSat pulse is shown, but a variety of pulses are known as the FatSat, and, for example, as shown in FIG. 3, a pulse is not particularly limited as long as the pulse functions as a fat saturation pulse such as the FatSat pulse including a plurality of RF pulses.

In imaging using a contrast agent, the MRI apparatus of the present embodiment continuously performs T1 weighted imaging in which such fat is suppressed over a time including a period from administration of the contrast agent to arrival of the contrast agent at a target site to continuously obtain an image of each phase. At this time, in a predetermined phase, a preparation pulse for suppressing a signal from the contrast agent that is present in a tissue in which the contrast agent easily moves and that is present out of the tissue which is the target of arrival of the contrast agent is added together with the FatSat pulse. The preparation pulse is used to suppress a contrast agent signal out of a target tissue, and there are some aspects. A specific example of the preparation pulse and a phase using the preparation pulse will be described in detail in the following embodiments.

Figure 4:
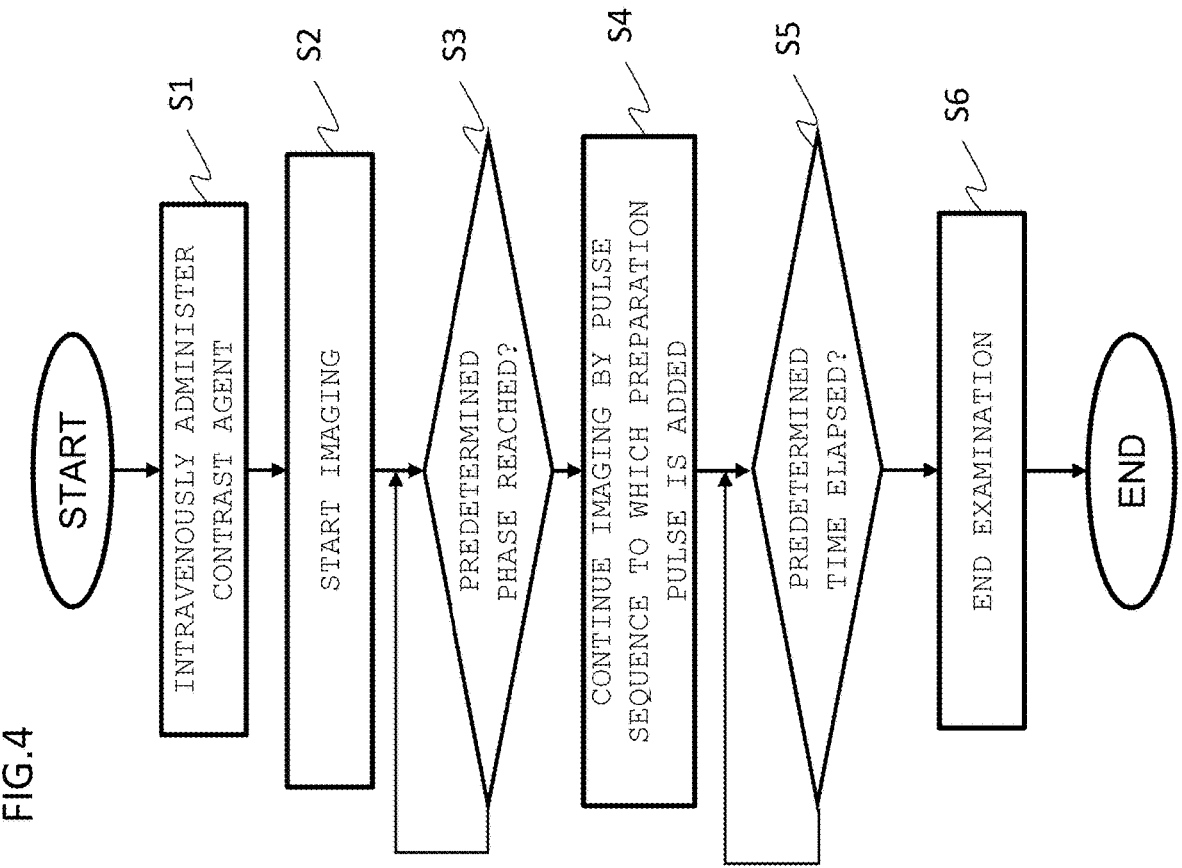
FIG. 4 is a diagram showing an embodiment of an imaging procedure of contrast-enhanced MRI according to the invention.

Next, a flow of processing of contrast-enhanced MRI using the MRI apparatus having the above-described configuration will be described with reference to FIG. 4. Here, imaging used for diagnosis of hepatocellular carcinoma and the like will be described as an example.

The contrast agent is administered to a subject positioned in an examination space (S1), and imaging of a predetermined site, for example, an abdomen is started, and is continuously performed (S2). The imaging is started after the administration of the contrast agent in FIG. 4, and may be started before the administration of the contrast agent. The pulse sequence used for the imaging is basically the same as the T1 weighted gradient echo pulse sequence (FatSat-RSSG) including the fat saturation pulse shown in FIG. 2. In the contrast-enhanced MRI, the 3D imaging is continuously repeated from before the administration of the contrast agent, the signal from the fat is suppressed, and a signal is obtained from a tissue in which a signal intensity is increased by the contrast agent.

The contrast agent administered to the subject (vein) reaches the target tissue via an artery, and is taken into the target tissue. During a process in which the contrast agent is taken into the target tissue, in a state (equilibrium state) in which while the contrast agent is taken into the target tissue, the contrast agent is also present in a surrounding tissue (tissue having diffusion and a flow), it is difficult to render only the target tissue with high luminance.

Therefore, a basic imaging sequence is repeated until a predetermined time elapses from the administration of the contrast agent to obtain an image, and the preparation pulse for suppressing the signal outside the target tissue is executed after the elapse of the predetermined time (S3, S4). The imaging including the preparation pulse can be continued even after the contrast agent has been taken into the target tissue through the equilibrium state (S4).

The contrast agent is taken into the target tissue, and after the predetermined time has elapsed (S5), an examination ends (S6). An imaging time after the contrast agent is taken into the target tissue may be set to the same time as that of the contrast-enhanced MRI in the related art. However, in an imaging procedure, since the target tissue can be rendered with high luminance before the contrast agent is almost entirely taken into the target tissue from the equilibrium state, a time may be short, and imaging after the contrast agent is taken into the targe tissue can be omitted.

When an abdomen is imaged, breath-holding imaging (intermittent imaging) may be performed. In such a case, positional deviation is corrected between the breath-holding imaging.

In this way, according to the present embodiment, in the equilibrium state until the contrast agent is taken into the target tissue, it is possible to improve a visualization capability of the target tissue by suppressing the signal from the tissue having a flow and diffusion of a blood vessel and the like around the target tissue, and to provide advanced diagnosis support information. Even when there is a difference in a capability of taking the contrast agent into the target tissue depending on the subject, it is possible to obtain an image in which the target tissue is rendered with the high luminance without taking a long time until the target tissue is captured.

Hereinafter, a specific embodiment will be described by taking, as an example, a case in which imaging is for the diagnosis of the hepatocellular carcinoma.

First Embodiment

The present embodiment is characterized in that a motion-sensitized driven-equilibrium (MSDE) pulse is used as a preparation pulse. It is known that the MSDE pulse is used as a pulse for suppressing the signal from the tissue having the flow, and the MSDE pulse is used in combination in T2*weighted imaging (NPL 2). In the present embodiment, the MSDE pulse is used in the predetermined phase of continuous contrast-enhanced MR imaging to emphasize a signal intensity difference between the phases, and a using method (control) of the MSDE pulse and an aim thereof are completely different from those known in the related art.

Figure 5:
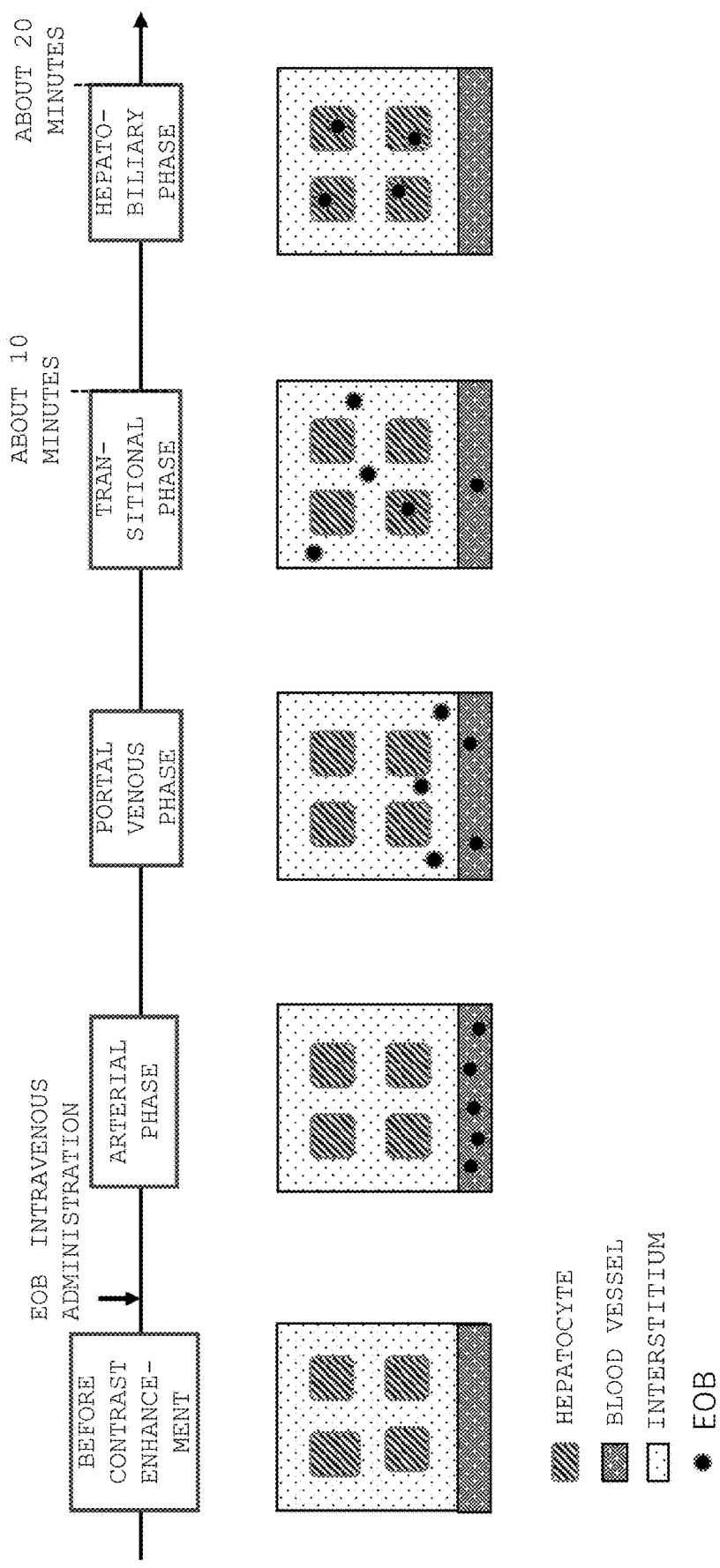
FIG. 5 is a diagram illustrating a phase change accompanied with movement of a contrast agent.

First, in the diagnostic imaging of the hepatocellular carcinoma, distribution and a signal change of the contrast agent (EOB) from administration of the contrast agent to arrival of the contrast agent at the target tissue (hepatocytes) will be described. As shown in FIG. 5, imaging phases include an arterial phase, a portal venous phase, a transitional phase, and a hepatobiliary phase as the contrast agent moves. A nutrient blood vessel of a liver is a portal vein, and a nutrient blood vessel of a tumor is an artery, and thus a signal intensity of the tumor is high in the arterial phase. The contrast agent reaching the tumor is gradually discharged, and the signal intensity of the tumor decreases as a phase changes in an order of the portal venous phase, the transitional phase, and the hepatobiliary phase. On the other hand, since a normal hepatocyte has a property of taking the EOB, the signal intensity increases in the order of the portal venous phase, the transitional phase, and the hepatobiliary phase.

The diagnosis of the hepatocellular carcinoma using the contrast-enhanced MRI is to visualize the tumor according to a fact that the signal intensity of the normal hepatocyte and the signal intensity of the tumor change reversely depending on the phase in this way. In the transitional phase and the hepatobiliary phase, there is a possibility that the EOB is distributed in all of the interstitial fluid, the blood vessel, and the cell. The signal of the hepatobiliary phase has a relatively low intensity with respect to the signals from the intercellular fluid and the blood vessel in the hepatocyte extracellular space, and diagnostic performance is lowered.

In the present embodiment, focusing on a fact that a degree of freedom of the diffusion of the EOB taken into the cell is lower than that of the EOB present in the interstitial fluid and the blood vessel, the MSDE pulse is applied as a pre-pulse to the FatSat+RSSG sequence to suppress a signal value of the hepatocyte extracellular space.

Figure 6:
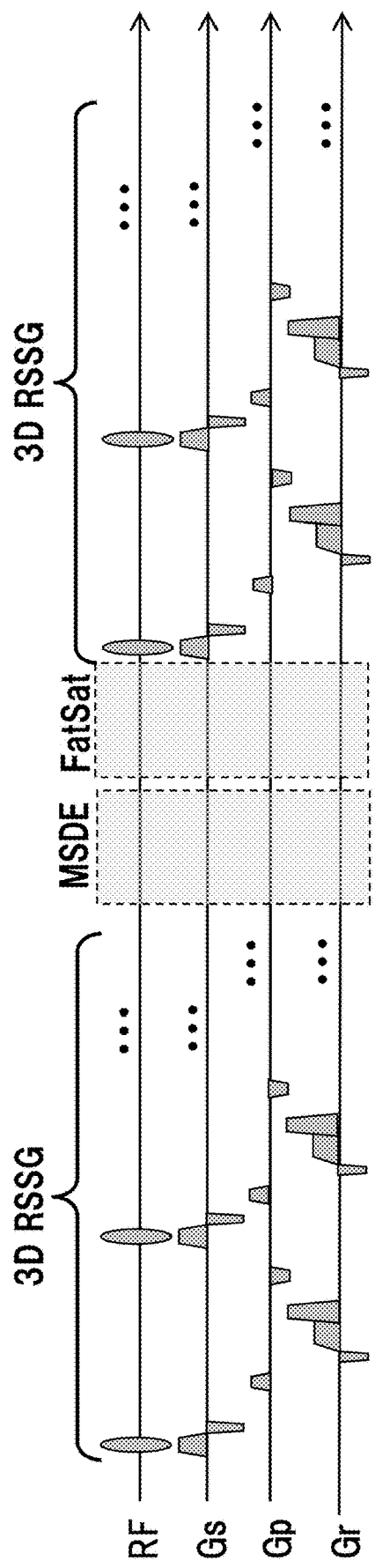
FIG. 6 is a diagram showing an example of a pulse sequence used in a first embodiment.

FIG. 6 shows an example of a pulse sequence including the MSDE pulse. As shown in FIG. 6, prior to the RSSG sequence, the MSDE pulse and the FatSat pulse are applied.

Figure 7:
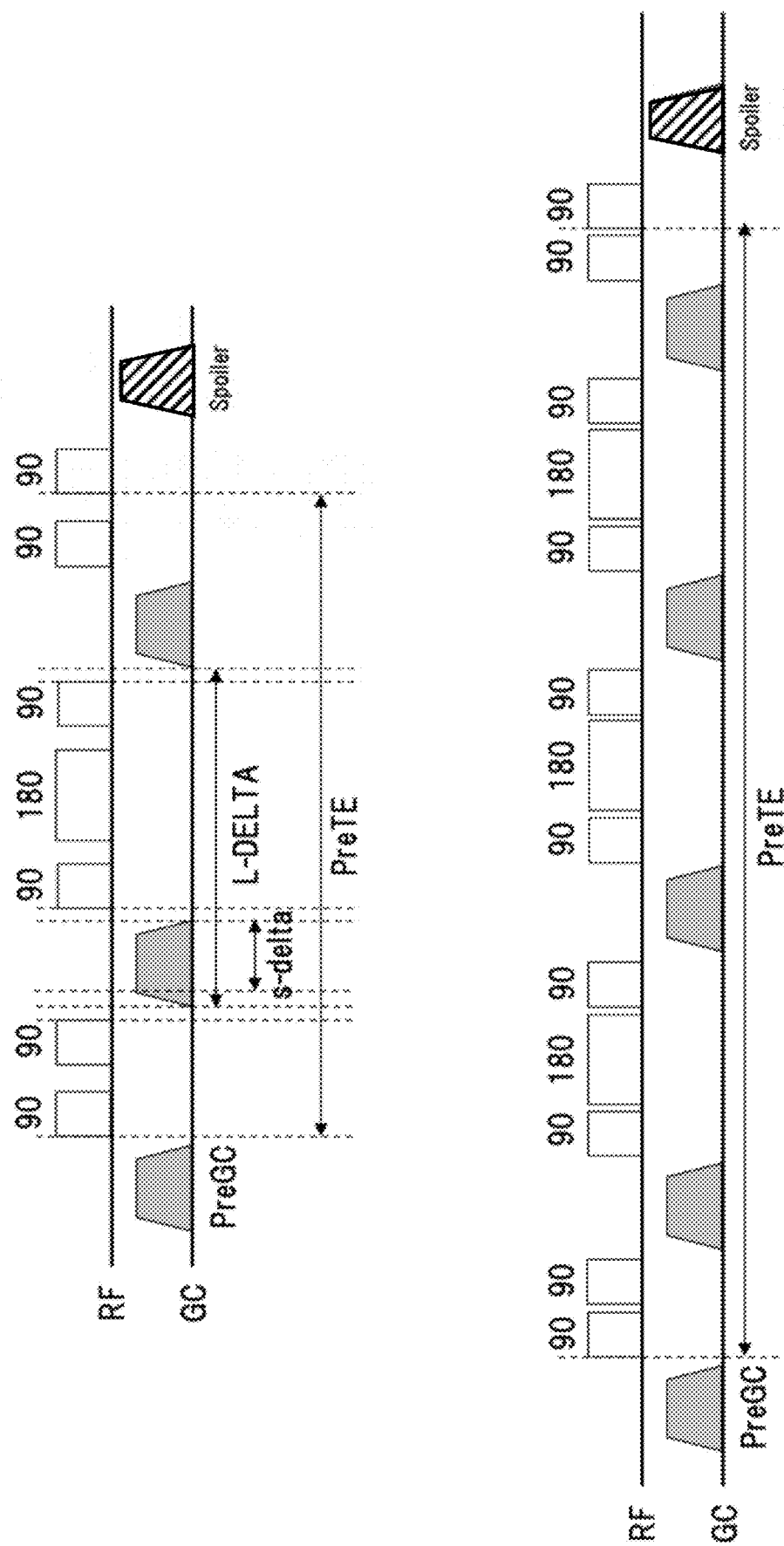
FIG. 7 is a diagram showing examples of an MSDE pulse.

Various methods are proposed for the MSDE, and any of them may be adopted. As an example, FIG. 7 shows examples of a composite pulse in which RF pulse groups and a motion probing gradient (MPG) pulse are combined. The number of RF pulse groups is set to three in an upper side in FIG. 7, and is set to five in a lower side in FIG. 7. In such an MSDE, the contrast can be adjusted by adjusting an applied intensity of an MPG pulse and an interval between pulses indicated by PreTE in the drawing. By increasing the number of the RF groups, there is a disadvantage that an SNR is lowered and the contrast is changed, whereas there is an advantage that robustness against non-uniformity of a static magnetic field intensity and an irradiation intensity is achieved, and the number of the RF groups is appropriately selected according to an object to be suppressed and other imaging conditions. The number may be selected by the user via a UI to be described later, or may be determined on an apparatus side.

In FIG. 6, the MSDE pulse and the FatSat pulse are not applied every time the RSSG is repeated, but may be applied once for a plurality of times of the RSSG. Further, the MSDE pulse may be applied to all phase encoding acquisition, or may be applied to only a low band of a k space which strongly contributes to the contrast and not applied to a high band to shorten the imaging time.

Although the MSDE pulse is applied before the FatSat pulse in FIG. 6, this order may be reversed. When the MSDE is applied before the FatSat, a signal suppression capability is lowered, and a fat saturation capability is improved. On the other hand, when the FatSat is applied before the MSDE, the fat saturation capability is lowered, but the signal suppression capability is improved. The user may select the order in accordance with which one of signal suppression and fat saturation is prioritized or the order may be fixed. When the user is allowed to set the order, the degree of freedom of the user can be improved. On the other hand, the order is fixed, work of the user can be reduced, and a workflow can be improved.

The amount of MSDE to be applied may be internally determined by the system based on the imaging condition or may be explicitly set by the operator, or an application ratio may be determined by preliminary measurement.

Figure 8:
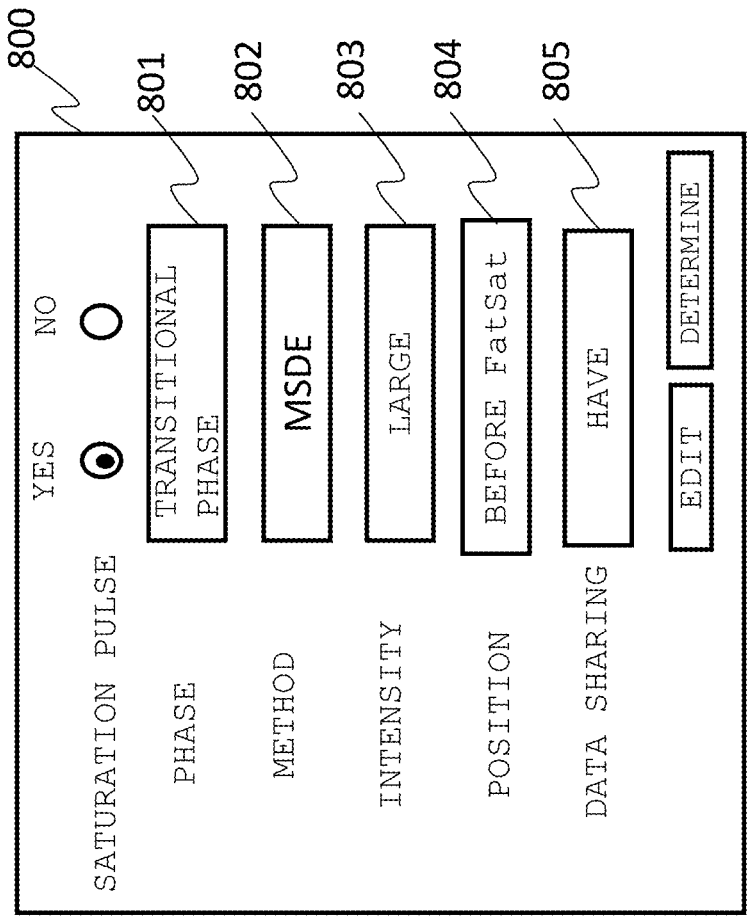
FIG. 8 is a diagram showing a flow of imaging (control) according to the first embodiment.

FIG. 8 shows an example of a GUI displayed on the display device due to the addition of the MSDE. In the example, for example, the computer (control unit) 20 causes the display device 30 to display a condition setting screen 800 related to the MSDE as an imaging condition setting screen set by the user in a hepatocellular carcinoma diagnosis examination using the contrast-enhanced MRI.

The condition setting screen 800 displays blocks 801 to 805 for receiving a button for instructing whether a saturation pulse is required, a phase for adding a pulse for reducing the EOB signal in the hepatocyte extracellular space, a type of the pulse, a degree of suppression (the intensity of the saturation pulse), a position to be inserted into the pulse sequence, and the like. A display mode is not limited to that illustrated in the drawing, and the user can specify at which phase the saturation pulse is to be used (for example, whether to use only the transitional phase or to use the transitional phase and the hepatobiliary phase) via the GUI of the blocks 801 to 803, can specify whether to use the MSDE or to use other pulses described later as the saturation pulse, or specify the intensity (to what extent the saturation is performed) in the case of using the saturation pulse. With respect to the block 804, when the fat saturation pulse is used, it is possible to specify to select whether to add the fat saturation pulse before or after the MSDE pulse. With respect to the block 805, it is possible to specify to select whether to add the fat saturation pulse to only a part (for example, a low frequency region) of the k-space data (in this case, the data of the high frequency region is shared with the data of the phase in which the data is collected to form an image) or to add the fat saturation pulse to the whole. Regarding the intensity of the saturation pulse, FIG. 8 shows a GUI for selecting large, medium, and small, but a value of the applied intensity may be directly input.

These conditions may be determined in a manner that the condition set in advance in the apparatus is presented and is approved or changed by the user.

Figure 9:
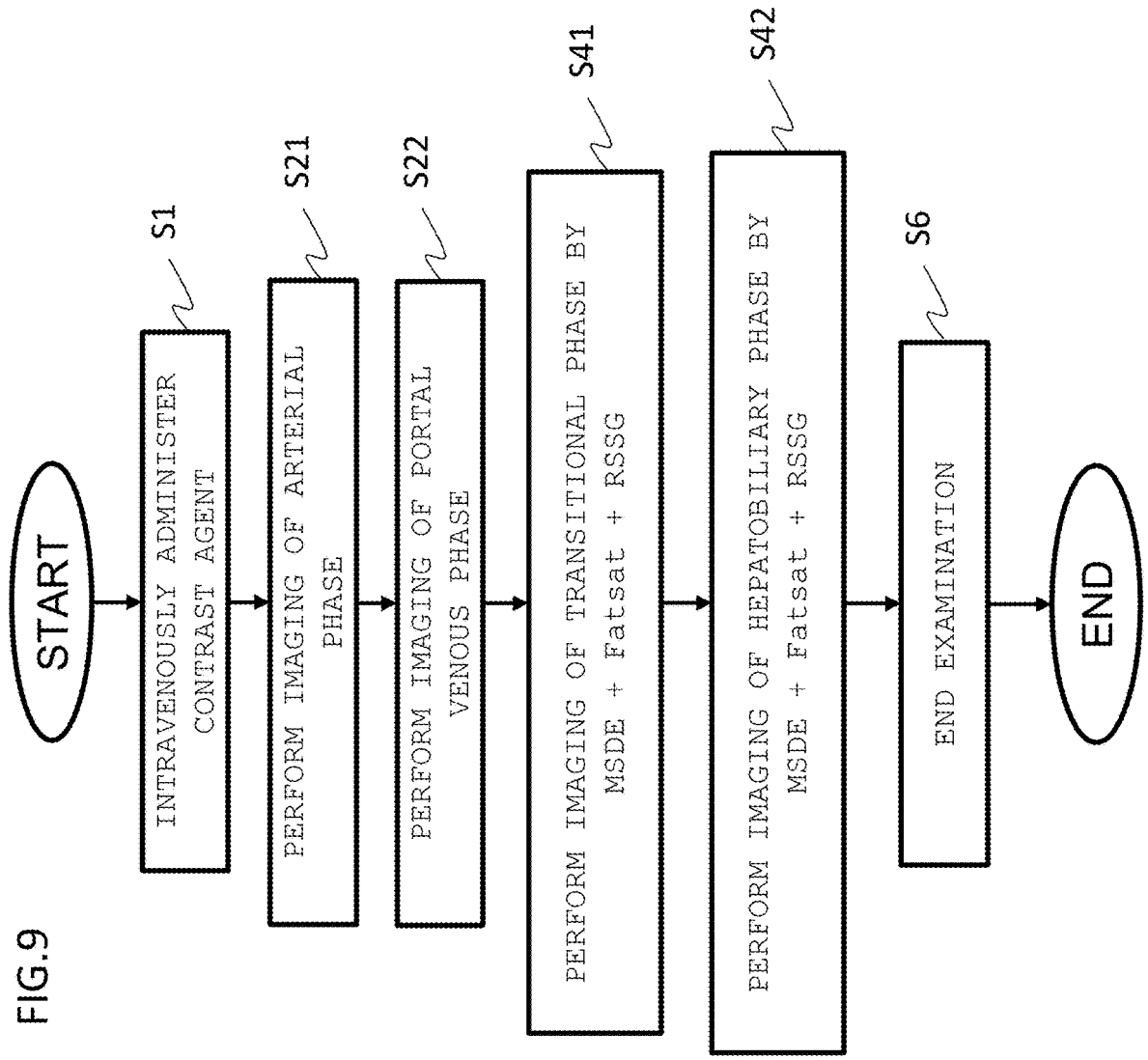
FIG. 9 is a diagram showing a flow of imaging according to the first embodiment.

Next, the imaging procedure of the present embodiment will be described with reference to FIG. 9. In FIG. 9, steps having the same contents as those in FIG. 4 are indicated by the same reference numerals.

First, the contrast agent (EOB) is administered to a vein of a subject, and imaging is started (S1). In the imaging of the arterial phase and the portal venous phase, the FatSat+ RSSG sequence shown in FIG. 2 is executed without applying the MSDE (S21, S22). At a time point of transition from the portal venous phase to the transitional phase, the imaging is performed while suppressing the signal from the hepatocyte extracellular space by adding the MSDE pulse (S41).

The time point of transition to the transitional phase may be determined in the system based on an empirical time, and imaging with MSDE added automatically may be started, or in dynamic imaging, image reconstruction is also continuously performed, and the image of each phase is displayed on the display device 30, and thus the user may make a determination from the image and specify a transition time.

In the subsequent hepatobiliary phase, imaging is also performed in the FatSat+RSSG sequence to which MSDE is added (S42). The computer (calculation unit) 20 performs the image reconstruction using the k-space data collected by the execution of the pulse sequence and sequentially displays the image on the display device 30. At this time, when the MSDE is applied only at the time of data collection in the low-frequency region of the k-space data, the image reconstruction is performed using data of phases collected without using the MSDE for data in the high-frequency region. Since the contrast of the image is determined in the low-frequency region of the k-space, an image in which the effect of the MSDE appears can be obtained even when the MSDE is added only to the low-frequency region of the k-space, and the imaging time can be shortened by limiting the data collection at the time of adding the MSDE to a part (low-frequency region) of the k-space data.

Thereafter, after a predetermined time has elapsed, the examination ends (S6).

According to the present embodiment, by applying the MSDE in the transitional phase, an image is obtained in which the signal resulting from the EOB which is present in the hepatocyte extracellular space is suppressed, and thus the diagnostic performance is improved. In general, the hepatobiliary phase is imaged about 20 minutes after the administration of the contrast agent. It takes a long time for a person whose liver function is lowered to take in and discharge the EOB. Therefore, while in general, it is said that the hepatobiliary phase occurs 20 minutes later, it cannot be determined whether the hepatobiliary phase actually occurs even 20 minutes later. However, an image in which the signal resulting from the EOB which is present in the hepatocyte extracellular space is suppressed is obtained by the application of the MSDE. Therefore, the diagnostic performance is improved.

Second Embodiment

In the first embodiment, imaging including the application of the MSDE is performed in the transitional phase, whereas in the present embodiment, the imaging including the application of the MSDE and the imaging to which the MSDE is not applied are performed, and it is determined whether to image the hepatobiliary phase according to a result of comparison between the two.

Figure 10:
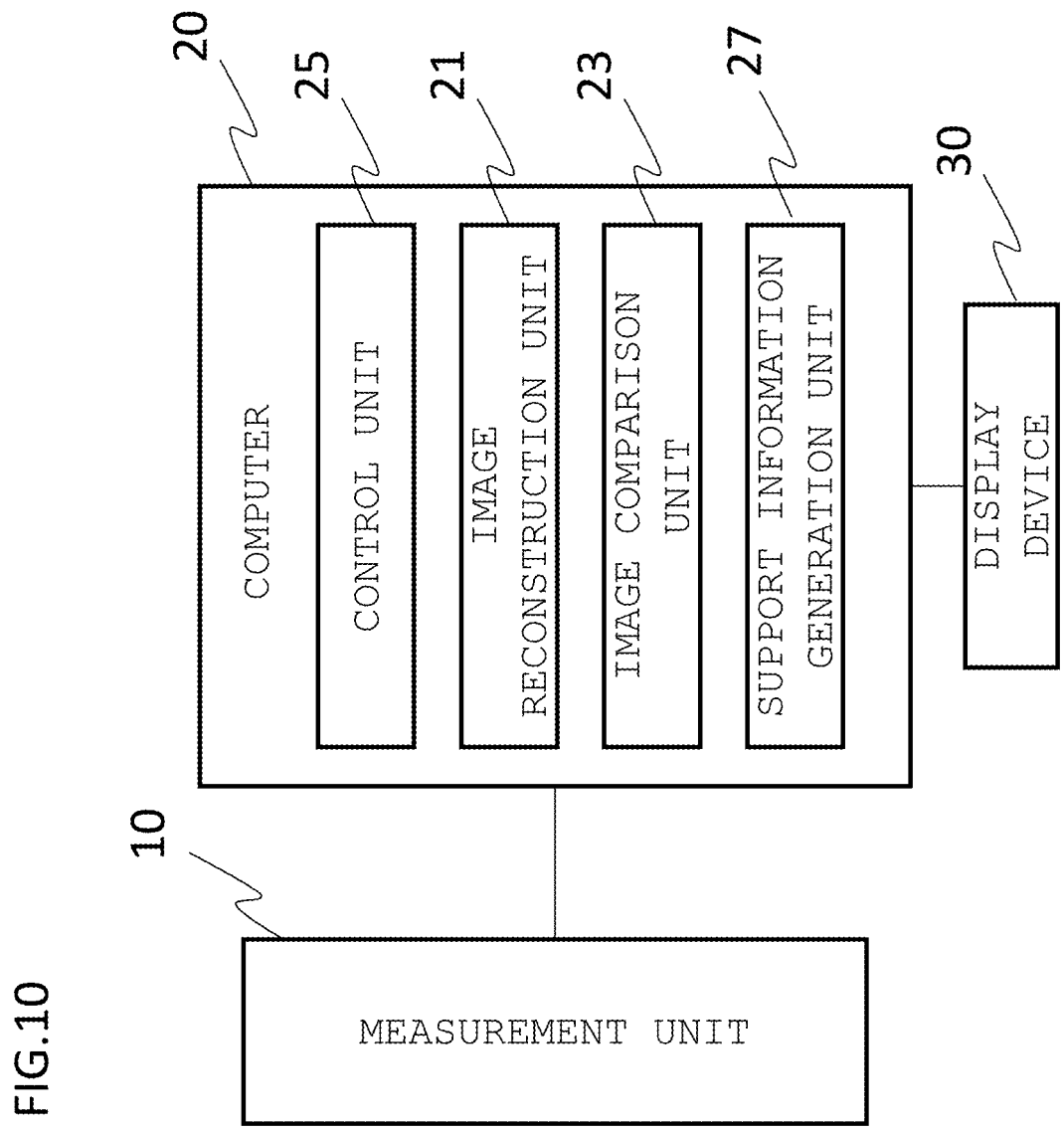
FIG. 10 is a functional block diagram of a computer according to a second embodiment.
Figure 11:
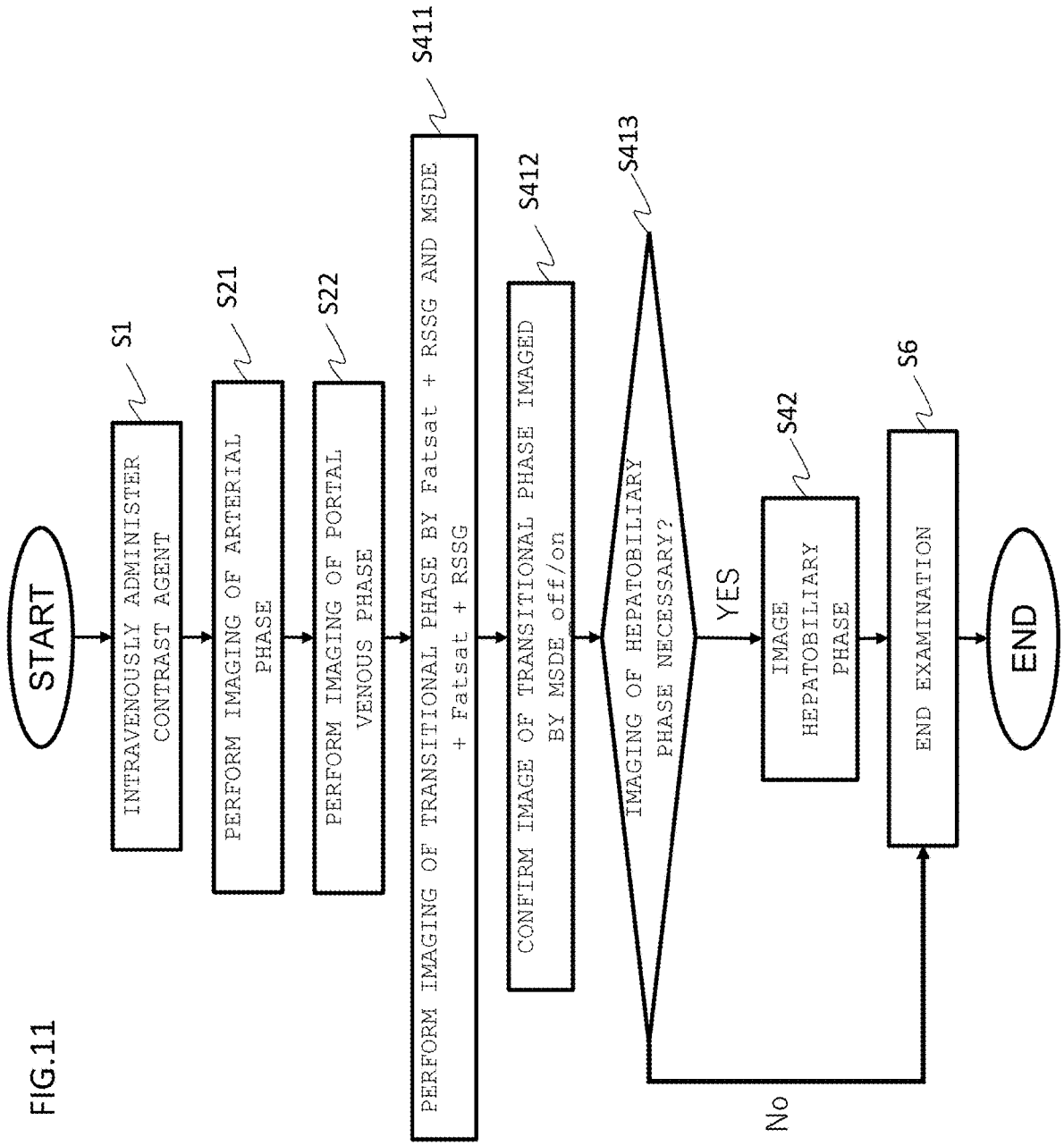
FIG. 11 is a diagram showing an example of a UI displayed on a display device.

Therefore, as shown in FIG. 10, the computer 20 for controlling the MRI apparatus 1 and calculating includes an image comparison unit (comparison unit) 23 in addition to an image reconstruction unit 21. The computer may further include a support information generation unit 27 that calculates diagnosis support information using a result of the image comparison unit 23. Among functions of the computer 20, a function of controlling the imaging unit 10, the display device, and the like is indicated as a control unit 25. Hereinafter, a procedure of the present embodiment will be described with reference to a flow of FIG. 11. In FIG. 11, the same steps as those in FIG. 9 are indicated by the same reference numerals, and redundant description thereof will be omitted.

In the present embodiment, similarly to the first embodiment, after the administration of the contrast agent (S1), in the imaging of the arterial phase and the portal venous phase, the FatSat+RSSG sequence is executed without applying the MSDE (S21, S22).

In the subsequent imaging of the transitional phase, the FatSat+RSSG sequence of no application of MSDE (MSDE_off) and the FatSat+RSSG sequence of the application of MSDE (MSDE_on) are repeatedly executed at a predetermined interval (S411). The repetition may be performed by using any one of a method of repeating application and non-application in a nested manner during imaging, and a method of repeating imaging one of application and non-application and then imaging the other. The former is advantageous in that the former is less likely to be affected by body motion.

When an image of MSDE_off and an image of MSDE_on are compared, a signal suppression effect by MSDE appears remarkably immediately after the start of imaging of the transitional phase, and a difference in a signal intensity is large. When EOB is incorporated into the hepatocytes as the time elapses, a suppression effect due to the application of MSDE does not appear as a difference in a luminance value. By displaying a comparison image of the MSDE_off/MSDE_on on the display device 30, a user can confirm a situation in which the EOB is taken into the hepatocytes (S412), and can determine whether to perform the subsequent imaging of the hepatobiliary phase (S413). For example, when it is determined that the signal intensity does not change and the EOB is substantially discharged from the hepatocyte extracellular space, the image of the hepatobiliary phase is obtained, and thus the imaging ends without imaging the subsequent hepatobiliary phase (S6).

Figure 12:
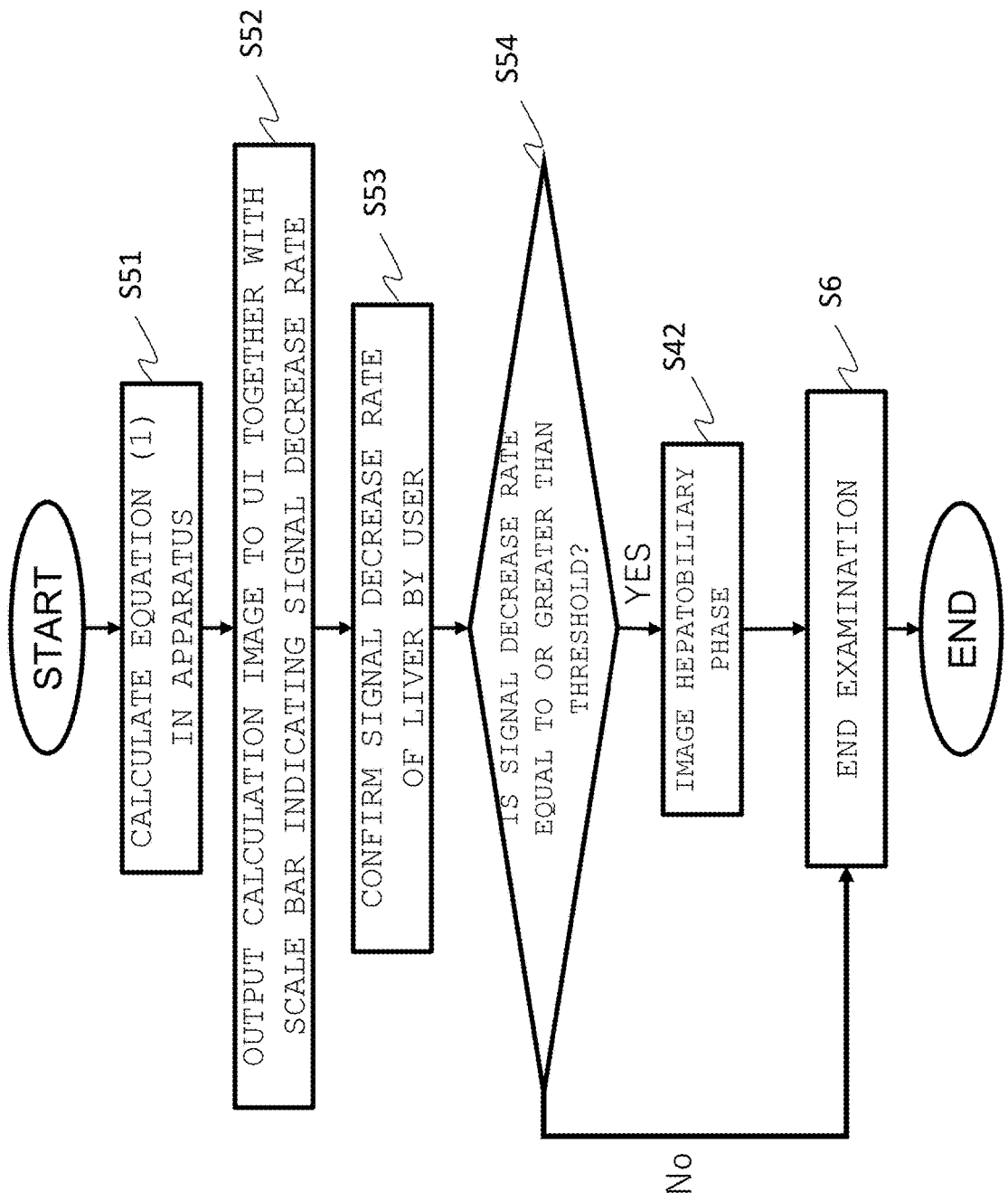
FIG. 12 is a diagram showing a flow of processing in the computer according to the second embodiment.

The determination of whether to perform imaging based on the display image may be automatically performed in the computer 20. FIG. 12 shows a processing flow in the computer 20 in this case. In the processing, steps S411 and S412 in FIG. 11 are replaced with steps S51 to S54 in FIG. 12.

First, when the image reconstruction unit 21 reconstructs an image using an echo signal collected by execution of the pulse sequence, the image comparison unit 23 compares an image obtained by MSDE_off with an image obtained by MSDE_on to calculate a decrease rate of the signal intensity (pixel value) (S51). The decrease rate of the signal intensity can be calculated by, for example, the following Expression (1).

$$\frac{SI_{MSDE\,off} - SI_{MSDE\,ON}}{SI_{MSDE\,off}} \qquad (1)$$

In the expression, $SI_{MSDE\_off}$ is the signal intensity of the image of MSDE_off, and $SI_{MSDE\_off}$ is the signal intensity of the image of MSDE_on.

As described above, when the EOB is taken into the hepatocytes as the time elapses, the suppression effect due to the application of the MSDE does not appear as a difference in the luminance value, and thus the decrease rate of the signal intensity decreases.

Figure 13:
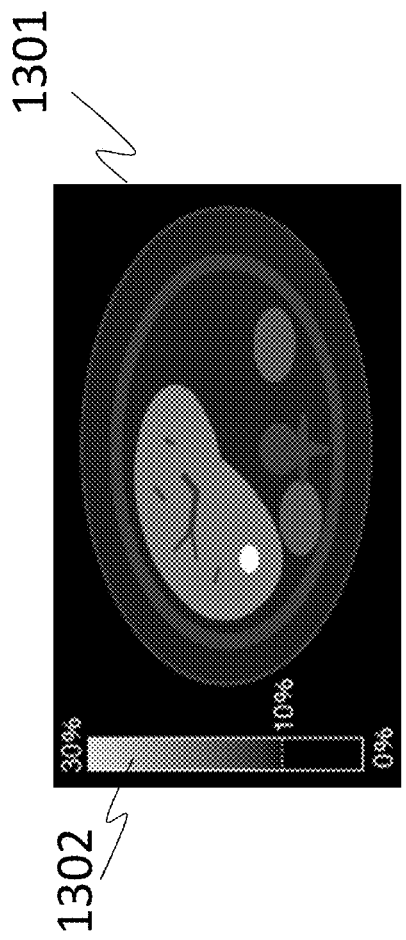
FIG. 13 is a diagram showing a result display example displayed on the display device.

The control unit 25 displays a signal decrease rate calculated by the image comparison unit 23 on the display device 30 (S52). A display example is shown in FIG. 13. In the display example, a map (calculation image) 1301 indicating a signal decrease rate of each pixel is displayed together with a scale bar 1302 indicating the signal decrease rate. The user can determine whether imaging of the next hepatobiliary phase is necessary by viewing such a result (S53), and a determination result may be accepted. When automatic determination is performed, a threshold is set in advance for the decrease rate of the signal intensity, and the control unit 25 determines whether to perform imaging based on the threshold (S54). That is, when the decrease rate of the signal intensity is lower than the threshold, it is considered that an image in which the hepatobiliary phase has already been rendered with high luminance is obtained, and thus the examination ends without imaging the hepatobiliary phase (S6). On the other hand, when the decrease rate of the signal intensity is equal to or higher than the threshold, the hepatobiliary phase is imaged with the MSDE_on as it is (S42). In the imaging of the hepatobiliary phase, by using MSDE_on, since an image in which a signal resulting from the EOB which is present in the hepatocyte extracellular space is suppressed is obtained, the diagnostic performance is also improved.

In the present embodiment, similarly to the first embodiment, a user setting relating to the saturation pulse may be accepted via the GUI as shown in FIG. 8, and the degree of freedom of the user can also be improved. An order of the MSDE pulse and the FatSat pulse may be fixed, and an examination flow can be simplified and shortened due to the fixing.

As described above, according to the present embodiment, in addition to the same effect as that of the first embodiment, two times of imaging of MSDE_off and MSDE_on are performed in the transitional phase, and it is determined whether to image the hepatobiliary phase from comparison of the images, so that an examination time can be shortened when it is unnecessary to image the hepatobiliary phase. In general, it is said that the hepatobiliary phase occurs 20 minutes after the administration of the contrast agent, but the imaging can be completed before the elapse of 20 minutes, which is a significant reduction of an imaging period.

Modification of Second Embodiment

In the present modification, the imaging of the MSDE_off and the imaging of the MSDE_on performed on the transitional phase are the same as those in the second embodiment. In this modification, however, comparison imaging of MSDE off/on is continuously performed even in imaging of the hepatobiliary phase. A result of the comparison imaging in the hepatobiliary phase can be used for evaluation of a hepatocyte function.

Figure 14:
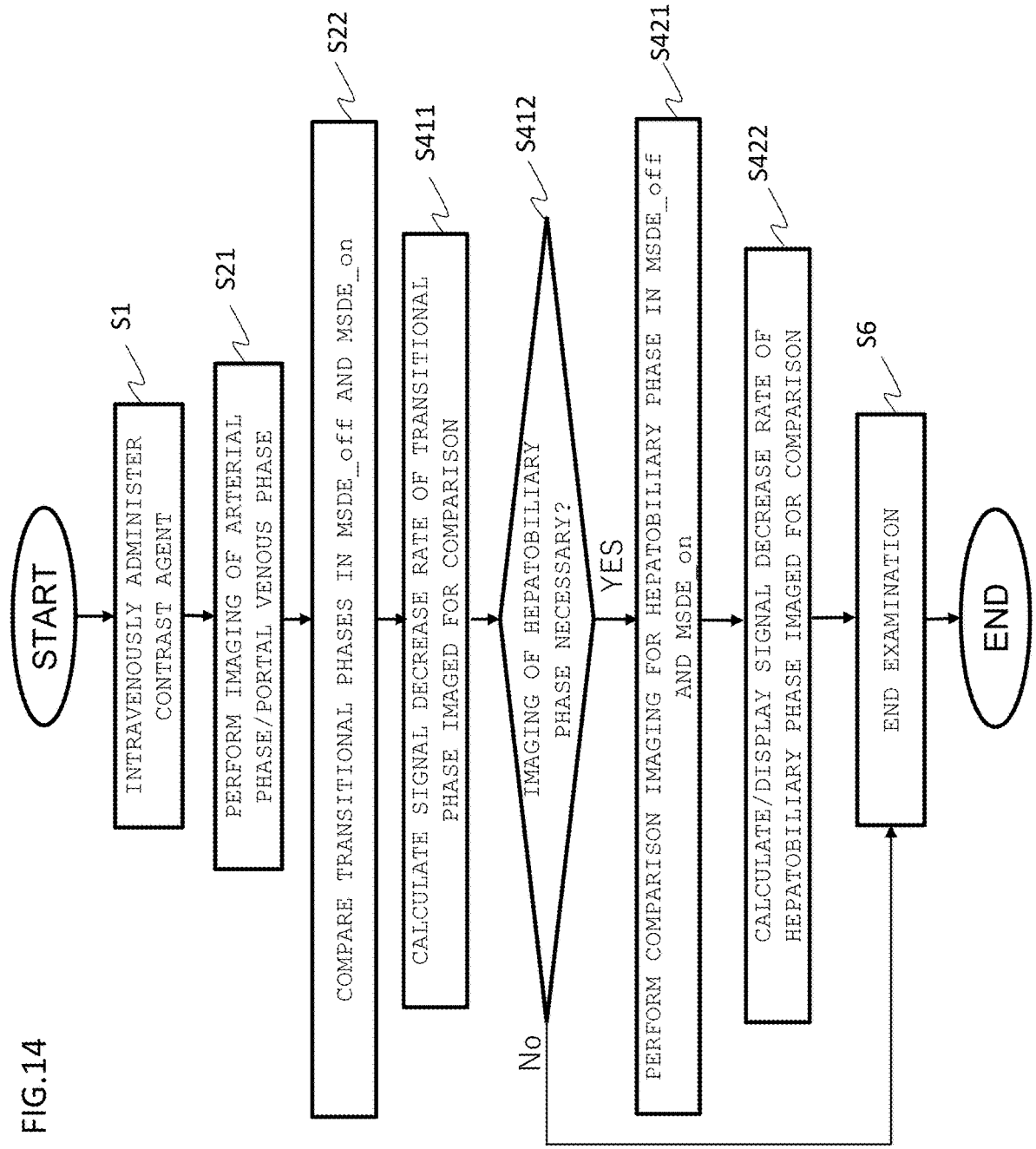
FIG. 14 is a diagram showing a flow of imaging according to a modification of the second embodiment.

FIG. 14 shows a flow of an imaging procedure of the present modification. In FIG. 14, the same steps as those in FIG. 11 are indicated by the same reference numerals, and redundant description thereof will be omitted. The present modification is also the same as the second embodiment in that it is determined whether to image the hepatobiliary phase based on the result of comparison imaging of MSDE_off/on in the transitional phase (S411 to S413), and that a user performs or a device automatically performs the determination.

In the present modification, when it is determined that the imaging of the hepatobiliary phase is necessary, the control unit 25 repeats the imaging of MSDE_off and the imaging of MSDE_on also in this imaging (S421), and the image comparison unit 23 calculates a signal decrease rate using the image obtained by the two times of imaging using Expression (1) described above (S422).

A fact that a change in the signal decrease rate is small is considered to be low in a capability of taking the EOB into the hepatocytes. Since the image comparison unit 23 causes the display device 30 to display the change in the signal decrease rate as illustrated in FIG. 13, the user can check the value of the signal decrease rate or a state of the change, and can use the value or the state as a diagnosis index. Alternatively, a qualitative liver function evaluation corresponding to the signal decrease rate may be registered in advance, the support information generation unit 27 may create the diagnosis support information based on registration information, and the qualitative liver function evaluation and the diagnosis support information may be displayed together.

In the above description, the signal decrease rate obtained for the hepatobiliary phase is presented as a determination index of the liver function, but the signal decrease rate obtained in the transitional phase may be used together or alone as the determination index of the liver function.

According to the present modification, in addition to the effect of the second embodiment, information effective for the liver function diagnosis can be presented to the user.

Third Embodiment

In the first and second embodiments, the MSDE pulse is used as the pulse for suppressing the signal from the EOB present outside the hepatocytes in the imaging of the transitional phase or the hepatobiliary phase, but a pre-pulse other than the MSDE pulse can be used as long as the pulse suppresses a signal from a tissue having a flow or diffusion. In the present embodiment, a motion probing gradient (MPG) pulse is used as such a pre-pulse.

An MPG pulse is a gradient magnetic field having a large intensity to be applied to generate a signal difference between spin and static spin of a tissue in which diffusion such as perfusion occurs in diffusion weighted imaging (DWI). In the present embodiment, in a predetermined phase of continuous imaging, that is, a transitional phase until the contrast agent reaches the hepatocytes and, if necessary, the hepatobiliary phase, the MPG pulse is used to reduce a signal from the EOB in the hepatocyte extracellular space.

Figure 15:
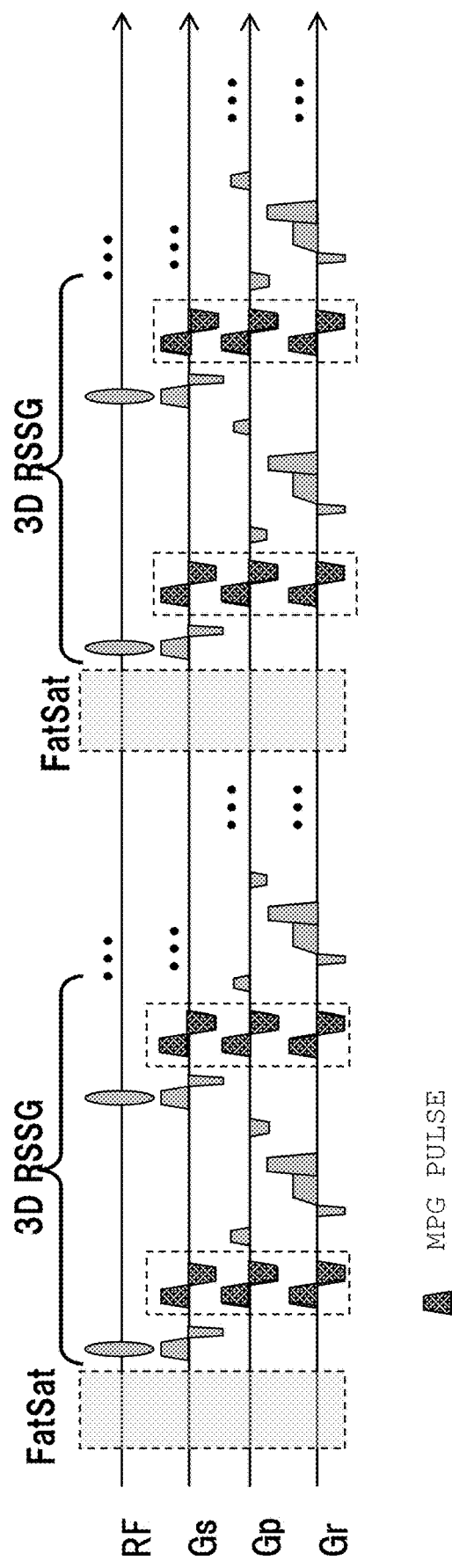
FIG. 15 is a diagram showing an example of a pulse sequence used in a third embodiment.

FIG. 15 shows a pulse sequence to which the MPG pulse is added. As illustrated, after an RF pulse is applied, a bipolar MPG pulse is applied in three axial directions. As in a case of the MSDE, the MPG pulse may be applied to each TR, or may be applied only when data of a k-space center is acquired. A b value, which is an index of the magnitude of the MPG pulse, may be one b value in each time phase of the transitional phase and the hepatobiliary phase, or imaging may be performed with the plurality of b values. When imaging is performed with the plurality of b-values, perfusion information can also be obtained as in IVIM.

Since TE is extended by applying the MPG pulse, contrast becomes worse compared with when the MSDE is applied.

Depending on whether the contrast priority or obtaining perfusion information, it may be possible to select whether to set the MSDE or the MPG pulse. Similarly to the first and second embodiments, data in the k-space high frequency area may be shared among the time phases to shorten imaging time. Although illustration is omitted, such user selection can be accepted via a GUI as shown in FIG. 8.

In the present embodiment, not only the MSDE pulse according to the first embodiment is replaced with the MPG pulse, but also the comparison imaging having no MPG pulse and having the MPG pulse in the transitional phase and the hepatobiliary phase may be performed as in the second embodiment and the modification thereof. Therefore, in addition to the effect of improving the diagnostic performance, similar effects of shortening the examination time and evaluating the liver function from the signal decrease rate are obtained as in the second embodiment. Further, according to the present embodiment, the perfusion information that is not obtained in the MSDE can be acquired by using the MPG pulse having the plurality of b values.

Fourth Embodiment

The above-described embodiments are examples in which the pre-pulse for suppressing the signal of the contrast agent present in the hepatocyte extracellular space is added to the pulse sequence for acquiring the signal from a target site, and the present embodiment suppresses the signal of the hepatocyte extracellular space by using arterial spin labeling (ASL).

Figure 16:
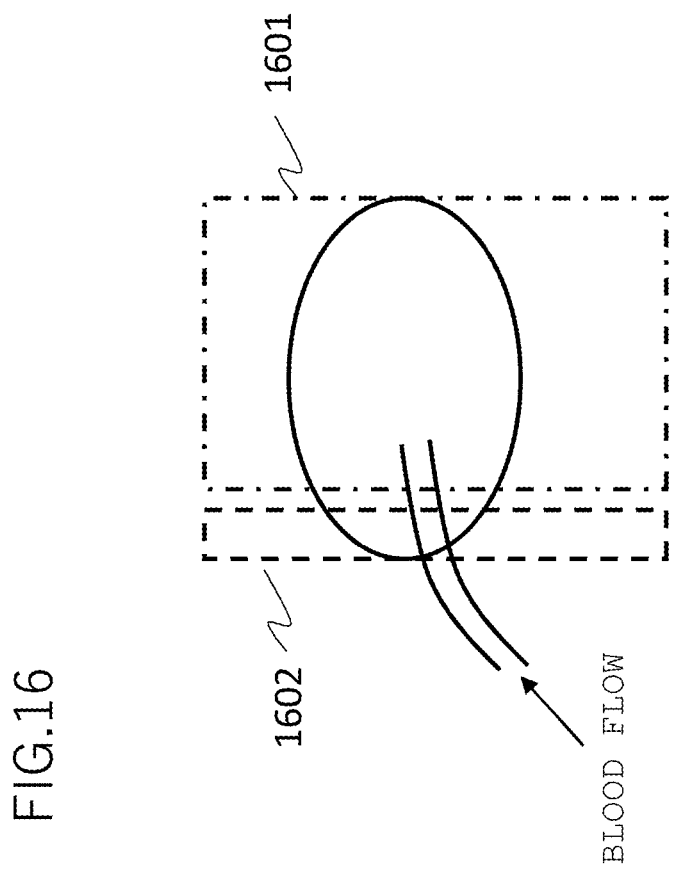
FIG. 16 is a diagram showing spin labeling according to a fourth embodiment.

The ASL is a method of exciting a region 1602 adjacent to the target site 1601 in advance as shown in FIG. 16 to reduce a signal by an MT effect of the labeled blood flowing into the target site from the adjacent region. As the labeling method, a PASL method using an inversion pulse, a pCASL method of continuously emitting RF to determine blood spin as a result, and the like are known, and any of the methods may be adopted.

In the present embodiment, imaging of the arterial phase and the portal venous phase is also performed by the gradient echo pulse sequence including the FatSat as shown in FIG. 2, which is similarly to the first and second embodiments. In the imaging of the transitional phase, the hepatic artery and the portal vein are spin-labeled, and imaging is performed after waiting for a predetermined delay time post labeling delay (PLD). Accordingly, a signal intensity of a liver parenchyma (a portion of the hepatocytes excluding the hepatocyte extracellular space) is lowered due to the magnetization transfer (MT) effect of the spin labeled blood. Accordingly, a signal intensity difference between the hepatocytes and the extracellular space is generated, and the signal from the hepatocytes excluding the signal from the hepatocyte extracellular space can be extracted.

However, since the reduction in the signal intensity by the MT effect of the spin labeling is a slight signal reduction of about 1% to 2%, an image not subjected to spin labeling may be acquired as a reference image, and a difference image may be output. Since it is possible to obtain an image in which the hepatocytes and hepatocyte extracellular space are rendered with different contrasts by using the difference image, information that can detect a tumor can be obtained from an image in which the hepatocytes are rendered with high luminance, and the perfusion information can also be obtained from the image in which the hepatocyte extracellular space are rendered with high luminance.

In the present embodiment, the comparison imaging in which the spin labeling is turned on/off at the time of imaging of the transitional phase may also be performed to determine whether to perform the subsequent imaging in the hepatobiliary phase, or the comparison imaging may be performed to obtain the information of the liver function at the time of imaging in the hepatobiliary phase, which is the same as in the other embodiments.

Accordingly, in the present embodiment, similarly to the embodiment using the pre-pulse such as the MSDE or the MPG pulse, effects such as improvement of diagnostic performance, evaluation of the liver function, and reduction of the examination time can be obtained. In the present embodiment, the perfusion information can be obtained.

What is claimed is:

1. A magnetic resonance imaging apparatus comprising:
   an imaging unit configured to apply a high-frequency magnetic field and a gradient magnetic field to a subject, collect a nuclear magnetic resonance signal generated from the subject, and generate an image of the subject, the imaging unit including a pulse sequence configured to acquire a T1 weighted image including a fat saturation pulse; and
   a control unit configured to control the imaging unit, wherein
   the control unit performs control in imaging to generate images of a plurality of phases having different arrival positions of a contrast agent by repeating the pulse sequence for a predetermined time from administration of the contrast agent to the subject by the imaging unit, and during the imaging and after elapse of the predetermined time, a preparation pulse configured to suppress a signal from the contrast agent present outside an arrival target tissue or cell of the contrast agent is added prior to the pulse sequence in a part of the plurality of phases.

2. The magnetic resonance imaging apparatus according to claim 1, wherein the imaging unit applies the preparation pulse either before or after the fat saturation pulse.

3. The magnetic resonance imaging apparatus according to claim 2, wherein the imaging unit uses an MSDE pulse or a bipolar MPG pulse as the preparation pulse.

4. The magnetic resonance imaging apparatus according to claim 1, wherein
   the imaging unit applies a spin labeling pulse as the preparation pulse to outside an imaging region.

5. The magnetic resonance imaging apparatus according to claim 1, wherein
   the pulse sequence configured to acquire the T1 weighted image is a 2D or 3D RF spoiling type gradient echo sequence.

6. The magnetic resonance imaging apparatus according to claim 1, wherein
   the imaging unit includes a comparison unit configured to execute a first pulse sequence to which the preparation pulse is added and a second pulse sequence to which the preparation pulse is not added in a part of the phases, and compare a signal collected by the first pulse sequence with a signal collected by the second pulse sequence.

7. The magnetic resonance imaging apparatus according to claim 6, wherein
   the control unit determines continuation of imaging of a next phase by the imaging unit according to a result of the comparison unit.

8. The magnetic resonance imaging apparatus according to claim 6, further comprising:

a support information generation unit configured to generate diagnosis support information for the subject based on a result of the comparison unit.

9. The magnetic resonance imaging apparatus according to claim 6, wherein
the control unit causes a display device to display at least one of a result of the comparison unit and diagnosis support information.

10. The magnetic resonance imaging apparatus according to claim 1, wherein
the control unit includes a user interface unit configured to receive at least one user setting of a type of the preparation pulse, a signal suppression intensity by the preparation pulse, and an addition position of the preparation pulse in the repetition of the pulse sequence.

11. The magnetic resonance imaging apparatus according to claim 1, wherein
the arrival target tissue of the contrast agent is a liver, and the plurality of phases includes an arterial phase, a portal venous phase, a transitional phase, and a hepatobiliary phase.

12. A control method for a magnetic resonance imaging apparatus that applies a high-frequency magnetic field and a gradient magnetic field to a subject according to a pulse sequence, collects a nuclear magnetic resonance signal generated from the subject, and generates an image of the subject, the control method comprising:
using a pulse sequence for acquiring a T1 weighted image including a fat saturation pulse to repeat the pulse sequence for a predetermined period of time from administration of a contrast agent to the subject to generate images of a plurality of phases having different arrival positions of the contrast agent; and
during imaging and after elapse of the predetermined time, adding a preparation pulse configured to suppress a signal from the contrast agent present outside an arrival target tissue or cell of the contrast agent prior to the pulse sequence in a part of the plurality of phases.

13. The control method for a magnetic resonance imaging apparatus according to claim 12, wherein in the repetition of the pulse sequence, the preparation pulse is added when a part of signals of k-space data made of the nuclear magnetic resonance signals is collected.

* * * * *